United States Patent [19]

Tsujii et al.

[11] Patent Number: 4,634,725
[45] Date of Patent: Jan. 6, 1987

[54] ROD-SHAPED POLYMER LATEX, ROD-SHAPED POLYMER FINE POWDER AND DISPERSION COMPRISING THE FINE POWDER DISPERSED IN NON-AQUEOUS MEDIUM

[75] Inventors: Kaoru Tsujii; Akira Yoshimatsu, both of Utsunomiya, Japan

[73] Assignee: KAO Corporation, Tokyo, Japan

[21] Appl. No.: 703,667

[22] Filed: Feb. 21, 1985

[30] Foreign Application Priority Data

Feb. 28, 1984 [JP] Japan ................................. 59-36380
Jun. 8, 1984 [JP] Japan ................................ 59-117511

[51] Int. Cl.$^4$ ............................................. C08J 3/02
[52] U.S. Cl. ..................................... 523/221; 521/29; 524/908; 526/909
[58] Field of Search ................ 523/220, 221; 521/29; 526/909; 524/904, 908

[56] References Cited

U.S. PATENT DOCUMENTS

| | | | |
|---|---|---|---|
| 4,157,328 | 6/1979 | Beyer | 523/220 |
| 4,264,676 | 4/1981 | Uzumaki | 521/29 |
| 4,447,566 | 5/1984 | Hruska | 523/221 |
| 4,474,907 | 10/1984 | Genba | 523/221 |

Primary Examiner—Paul R. Michl
Attorney, Agent, or Firm—Oblon, Fisher, Spivak, McClelland & Maier

[57] ABSTRACT

A finely powdered polymer latex in the rod-like form having a major axis of from 0.1 to 100 microns and a minor axis of below $\frac{1}{3}$ times the major axis. When the particles are dispersed in water at a concentration of 15 wt %, the thixotropy index, $\eta 3/\eta 30$ is not less than 1.5.

The polymer powder of the above size and configuration is useful in various fields including paint binders, diagnostic means and cosmetics.

The polymer latex is prepared by solubilizing a polymerizable monomer in rod-shaped micelles, and polymerizing the monomer while keeping the rod-shaped micelle structure.

9 Claims, 5 Drawing Figures

ROD-SHAPED POLYMER LATEX, ROD-SHAPED POLYMER FINE POWDER AND DISPERSION COMPRISING THE FINE POWDER DISPERSED IN NON-AQUEOUS MEDIUM

BACKGROUND OF THE INVENTION (i) Field of the Invention

This invention relates to rod-shaped polymer lattices comprising latex particles having a novel rod shape, rod-shaped polymer fine powders, and dispersions comprising the fine powder in non-aqueous media.

(ii) Description of the Prior Art

Polymer latices or emulsions have been widely utilized as binders for paints, adhesives, paper coatings, immunodiagnostics, sizes for clothes. These lattices are, in most cases, produced by emulsion polymerization and comprise particles which are spherical in shape. Recently, there has been proposed a method of preparing a polymer latex other than the emulsion polymerization in which a polymer latex called soap-free emulsion is prepared without use of any surface active agents. In this case, the particles are nothing but spheres. Thus, the shape of the particles currently utilized as polymer lattices is spherical in all cases. On the other hand, attempts have been recently made to change the shape of latex particles. In fact, there have been proposed several odd-shaped lattices. These particles can be broadly classified according to the shape thereof as follows.

(1) Core-shell type particles in which polymer particles have different components of the core and shell (Japanese Laid-open Patent Application No. 55-55414).

(2) Confetti particles in which polymer particles have irregularities on the surfaces thereof (Collection of Polymer Theses, Vol. 36 (1979)).

(3) Localized particles in which different types of polymers suffer phase separation in a latex (Kagaku Giken Report Vol. 35, 1980).

In all the cases, however, spherical latex particles are provided as nuclei and are covered with arbitrary polymers by seed polymerization. Accordingly, latex particles are considered to be spherical particles of lattices which are somewhat varied or modified in shape. According to the conventional polymerization methods, there could not be obtained lattices comprising particles which are not spherical in shape but are so shaped as to enhance the function thereof.

There is a high demand for techniques of imparting higher performance to lattices by changing the shape of lattices paticles. For instance, when polymer lattices are used as paint binders, good thixotropic properties are required. With known spherical lattices, however, such a requirement cannot be satisfied, so that it is usual to add other types of polymer compounds capable of imparting thixotropic properties to the lattices. However, if it is possible to permit paints to develop thixotropic properties by changing the shape of latex particles, addition of the thixotropy-imparting polymers becomes unnecessary. With diagnostic lattices, latex particles having a large surface area are required in order to increase an adsorption of antigen or antibody and enhance the sensitivity to immune reaction. As is well known, sphere is in such a shape that has the smallest specific surface area. In this sense, spherical latex particles are not suitable for use in lattices for diagnosis.

Rod-shaped inorganic fine powders such as of kaolin, goethite, γ-iron oxide, wollastonite, light calcium carbonate, and the like have been widely utilized as pigments or thickeners for make up cosmetics, paints, paper coatings and the like. However, these materials are all natural inorganic materials, so that their properties are substantially similar to one another and there has never been known any material which is substantially different in nature from other materials. With regard to surface properties, for example, these known materials are hydrophilic in nature. Accordingly, it is the usual practice that if hydrophobicity is required as with loading pigments for makeup cosmetics, the pigment is inevitably treated to impart the hydrophobicity thereto. Moreover, the inorgannic materials are great in specific gravity, so that when they are used as dispersions in non-aqueous media (e.g. oil paints), it is necessary to prevent the materials from setting. In addition, these natural products have the problem that a constant quality cannot be ensured. For instance, with wollastonite, their major axis distributes from 1 $\mu$m to about 500 $\mu$m. Moreover, because of the presence of impurities, these natural rod-shaped inorganic powders have to be purified through a number of steps, with various problems accompanied at the time of effective utilization of these natural fine powders.

SUMMARY OF THE INVENTION

Under these circumstances, the present inventors made intensive studies to obtain polymer lattices comprising latex particles of a novel shape and rod-like or rod-shaped polymer fine powders which have more uniform sizes than natural inorganic powders and overcome the drawbacks of the natural inorganic powders. As a result, it was found that latex particles in polymer latices which were obtained by the solubilization polymerization method described hereinafter had a large surface area and had high thixotropic properties. When water and, if necessary, a surface active agent used were removed from the polymer lattices, rod-shaped fine powder could readily be obtained. The fine powder could be dispersed in nonaqueous media to obtain dispersions. The present invention is accomplished on the basis of the above finding.

According to one aspect of the invention, there is provided a rod-shaped polymer latex which comprises latex particles having a major axis of from 0.1 to 100 $\mu$m and a minor axis of less than ⅓ the major axis, an aqueous dispersion of the particles at a concentration of not largerthan 15 wt % having a thixotropy index, $\eta3/\eta30$, of not less than 1.5 in which $\eta3$ and $\eta30$, respectively, represent viscosities when measured by means of the Brookfield viscometer at 3 and 30 r.p.m.

According to another aspect of the invention, there is also provided a rod-shaped polymer fine powder having a major axis of from 0.1 to 100 $\mu$m and a minor axis of less than ⅓ the major axis. Also, there is provided a dispersion comprising the fine powder dispersed in a non-aqueous medium.

DETAILED DESCRIPTION OF THE INVENTION AND PREFERRED EMBODIMENTS

Figure 1:
FIG. 1 is an electron microphotograph showing the structure of latex particles of the invention obtained using sodium hexadecenylsuccinate (degree of neutralization of 0.7)
Figure 2:
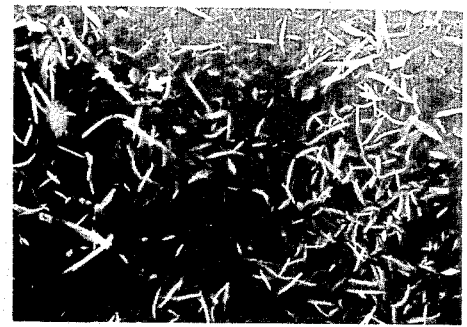
FIG. 2 is an electron photomicrograph showing the structure of latex particles of the invention obtained using N,N-dimethyl-N-(carboxymethyl)octadecylammonium inner salt (molar fraction of 0.5) and sodium octadecylsulfate (molar fraction of 0.5)
Figure 3:
FIG. 3 is an electron microphotograph showing the structure of latex particles of the invention obtained using octadecyltrimethylammonium halogenated benzoate.
Figure 4:
FIG. 4 is a scanning electron microphotograph showing the structure of latex particles obtained using ethylene oxide adduct of didodecylglycerine ether (moles of added ethylene oxide: 20)

The rod-shaped polymer lattices according to the invention may be obtained by polymerizing various polymerizable monomers indicated hereinafter and have such a shape that a minor axis of the latex particles is less than ⅓ the major axis. In general, the major axis is not larger than 100 μm. Preferably the major axis is in the range of from 0.1 to 15 μm and the minor axis is in the range of from 0.01 to 0.3 μm.

According to the present invention, the rod-shaped polymer lattices are prepared by solubilizing a polymerizable monomer in rod-shaped micelles, and polymerizing the monomer while keeping the rod-shaped micelle structure.

The solution comprising the rod-shaped micelles may be defined in terms of spinnability of liquid, flow-induced optical anisotropy, Weissenberg effect or the like, but is defined most accurately in terms of dynamic elastic modulus. Examples of such solutions are aqueous surface active agent solutions whose dynamic elastic modulus is not less than 0.01 dyne/cm² in a frequency range of from 0.05 to 1.0 Herz. Although the dynamic elastic modulus of the aqueous surface active agent solution may be over 0.01 dyne/cm², inclusive, the modulus is preferably in the range of from 0.5 to 10 dyne/cm². If the dynamic elastic modulus is less than 0.01 dyne/cm², the rod-shaped micelles are broken by the addition of monomers. On the other hand, when the modulus is greater than 10 dyne/cm², the rod-shaped polymer latex can be formed but agitation at the time of the production becomes difficult.

Surface active agents which satisfy the above requirements include those agents indicated in (a) through (f) below.

(a) Compounds of the following general formula

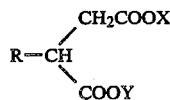

in which R represents a hydrocarbon group having from 6 to 24 carbon atoms, and X and Y independently represent a hydrogen atom, an alkali metal, ammonium, an alkanolamine having from 2 to 3 carbon atoms, or a basic amino acid.

(b) Compounds of the following general formula

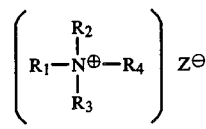

in which $R_1$ represents a hydrocarbon group having from 8 to 24 carbon atoms, $R_2$, $R_3$ and $R_4$ independently represent a hydrocarbon group or a hydroxyhydrocarbon group having from 1 to 3 carbon atoms, or a benzyl group, and $Z^\ominus$ represents a counter anion.

(c) Compounds of the following general formula

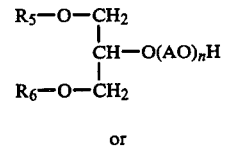

or

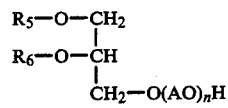

in which $R_5$ and $R_6$ independently represent a hydrocarbon group having from 6 to 24 carbon atoms, n is an integer of from 1 to 50, and A represents one or more of hydrocarbon groups each having from 2 to 4 carbon atoms.

(d) Surface active compositions comprising the following two ingredients (A) and (B) in a ratio by weight of 100:20 to 30:100.

(A)
(1) $RSO_3X_1$
(2) $RSO_4X_1$
(3) $RO(AO)_{n1}SO_3X_1$, or

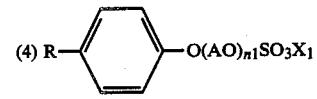

in which R represents a hydrocarbon group having from 6 to 24 carbon atoms, $n_1$ represents an integer of from 1 to 20, A represents a hydrocarbon group having from 2 to 4 carbon atomx, $X_1$ represents ammonium, an alkali metal, an alkaline earth metal, an alkanolamine having from 2 to 3 carbon atoms, or a basic amino acid.

(B)

(1) 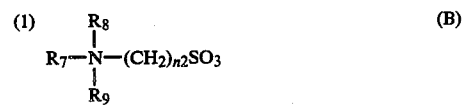

(2) 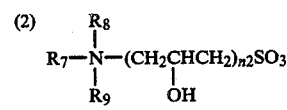

(3) 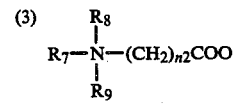

(4) 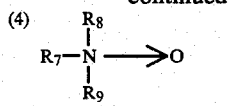

(5) 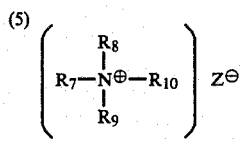

in which $R_7$ represents a hydrocarbon group having from 6 to 24 carbon atoms, $R_8$, $R_9$ and $R_{10}$ independently represent a hydrocarbon group or hydroxyhydrocarbon group, each having from 1 to 3 carbon atoms, or a benzyl group, n2 is an integer of from 1 to 10, and $Z^\ominus$ represents a counter anion.

(e) Compounds of the following general formula

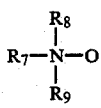

in which $R_7$, $R_8$ and $R_9$ have, respectively, the same meanings as defined before.

(f) Compounds of the following general formula

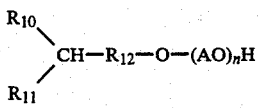

in which $R_{10}$ represents a hydrocarbon group having from 6 to 24 carbon atoms, $R_{11}$ represents a hydrocarbon group having from 1 to 24 carbon atoms, $R_{12}$ represents a hydrocarbon group having from 1 to 4 carbon atoms, A and n have, respectively, the same meanings as defined before.

Preferable examples of these surface active agents include: partially neutralized products of alkyl or alkenylsuccinic acid whose hydrocarbon moiety has from 6 to 24 carbon atoms such as, for example, dodecylsuccinic acid, octadecylsuccinic acid, dodecenylsuccinic acid, octadecenylsuccinic acid and the like; mixtures of N,N-dimethyl-N-(carboxymethyl)alkylammonium inner salts whose hydrocarbon moiety has from 6 to 24 carbon atoms and sodium alkylsulfates whose alkyl moiety having from 6 to 24 carbon atoms; mixtures of N,N-dimethyl-N-(3-sulfopropyl)alkylammonium inner salts whose alkyl moiety has from 6 to 24 carbon atoms and sodium alkylsulfates having from 6 to 24 carbon atoms; alkyltrimethylammonium halogenated benzoates or salicylates whose hydrocarbon moiety has from 6 to 24 carbon atoms; ethylene oxide adducts of dialkyl glycerine ethers whose hydrocarbon moiety has from 6 to 24 carbon atoms; and ethylene oxide adducts of Guerbet alcohols.

In the practice of the invention, polymerizable monomers used may be any monomers which are used in ordinary polymerization reactions such as, for example, radical polymerization reactions, polycondensation reactions, and polyaddition reactions.

The polymerizable monomers used in the present invention are described below with regard to the radical polymerization, polycondensation and polyaddition reactions along with the preparation of rod-shaped polymer lattices.

(i) Radical Polymerization

Useful polymerizable monomers are any known monomers which are ordinarily used for emulsion polymerization and include, for example, ethylenically unsaturated monomers such as ethylene, propylene, isobutene, butene-1 and the like; aromatic vinyl monomers such as styrene, α-methylstyrene, vinyltoluene, halogenated styrene, divinylbenzene and the like; acrylic esters whose alkyl group has from 1 to 20 carbon atoms such as ethyl acrylate, butyl acrylate, 2-ethylhexyl acrylate and the like; methacrylic esters whose alkyl group has from 1 to 20 carbon atoms such as methyl methacrylate, butyl methacrylate, lauryl methacrylate and the like; vinyl esters such as vinyl acetate, vinyl propionate and the like; vinyl ethers having from 1 to 20 carbon atoms such as ethyl vinyl ether, butyl vinyl ether and the like; vinyl ketones having from 1 to 20 carbon atoms in an alkyl group such as methyl vinyl ketone, ethyl vinyl ketone and the like; vinyl cyanide monomers such as acrylonitrile, methacrylonitrile and the like; vinyl halides such as vinyl chloride, vinyl bromide, vinylidene chloride, vinylidene bromide and the like; and aliphatic conjugated dienes such as vinylidene halides, 1,3-butadiene, 2-methyl-1, 3-butadiene and the like. These monomers may be used singly or in combination of two or more. In addition, the above monomers may be copolymerized with maleic anhydride, water-soluble monomers, styrene sulfonic acid or sulfonates, vinyl naphthalenesulfonic acid or naphthalenesulfonates and acrylates.

The most preferable procedure for preparing rod-shaped polymer latices comprises the steps of preparing an aqueous solution having viscoelasticity by charging a surface active agent into a reactor in which water is placed, adding a polymerizable monomer and, if necessary, a radical polymerization initiator under heating and agitating conditions while keeping the viscoelastic property of the solution, thereby starting the polymerization, and further adding the monomer gradually under such conditions that the dynamic elastic modulus of the aqueous solution of the surface active agent is within the range defined before.

The radical polymerization initiators include, for example, persulfates such as potassium persulfate, sodium persulfate, ammonium persulfate and the like; azo compounds such as mineral acid salts of 2,2'-azobis(2-amidinopropane), azobiscyanovalerianic acid and alkali metal and ammonium salts thereof; and peroxide compounds such as benzoylperoxide, laurylperoxide and the like; Redox initiators such as tartaric acid-hydrogen peroxide, rongalite-peroxides, ascorbic acid-peroxides and the like. Of these, salts of 2,2'-azobis(2-amidinopropane) and mineral acids are preferred when cationic surface active agents are used in the polymerization system, and persulfates are preferred in other polymerization systems. The amount of radical polymerization initiator is in the range of 0.1 to 5 parts by weight (hereinafter referred to simply as parts), preferably from 0.1 to 3 parts, per 100 parts of the monomer used.

The reaction temperature should be a maximum temperature such that a dynamic elastic modulus can be maintained in a reaction solution and is preferably in the range of from 50° to 90° C. The time required for the polymerization depends on the type, composition and concentration of monomer, the concentration of radical polymerization initiator, and the polymerization temperature and is preferably within a range of from 5 to 50 hours.

(ii) Polycondensation

Polycondensation monomers useful for the purpose of the invention may be any known monomers which are used for interfacial polycondensation or low temperature polycondensation. Of these, monomers capable of producing polyamides and polyesters are preferred. For instance, acid components used to prepare polyamides include alkylenedicarboxylic acids comprising hydrocarbon moieties having from 1 to 24 carbon atoms, dimer acids, phthalic acids such as terephthalic acid, isophthalic acid and the like, aromatic polyvalent carboxylic acids, acid chlorides or acid anhydrides corresponding to cyclic aliphatic polyvalent carboxylic acids, thio esters of dicarboxylic acids, and the like. Diamine components include, for example, aliphatic polyvalent amines comprising hydrocarbon having from 1 to 24 carbon atoms, such as alkylenediamines, alkylenetriamines and the like, aromatic polyvalent amines such as phenylenediamine, 4,4'-diaminophenyl ether and the like, polyvalent amines having heterocyclic rings, and the like.

Alcohol components used to prepare polyesters include, for example, ethylene glycol condensates having hydrocarbon moieties having from 1 to 24 carbon atoms, such as alkylene diols, bis-β-hydroxyethyl terephthalate and the like, aromatic polyvalent alcohols such as hydroquinone, bisphenol A and the like, polyols such as glycerine derivatives, and the like. The acid components are those compounds as described above with respect to polyamides. As a matter of course, other types of monomers may also be used in the practice of the invention. The monomers indicated above may be used singly or in combination.

For the preparation of rod-shaped polymer lattices, a surface active agent is added to a reactor in which water is placed and agitated to solubilize an acid component therein, followed by adding an aqueous solution of a diamine or alcohol. Alternatively, separate solutions of both components in organic solvents may be, respectively, added to and solubilized in aqueous solutions of surface active agents, and then combined together. Where a monomer used is solid, it is preferable to dissolve the solid monomer in an organic solvent and solubilize the monomer in rod-shaped micelles along with the solvent for subsequent polycondensation. The solvents used for these purposes should conveniently be insoluble in water and, preferably, benzene, toluene and xylene are used. The reaction temperature is a temperature such that a dynamic elastic modulus can be maintained in a reaction solution and is preferred to be within a range of from −10° to 50° C. The reaction time may vary depending on the type, composition and concentration of monomer and the reaction temperature and is preferably in the range of from 2 to 60 minutes.

(iii) Polyaddition

The addition-polymerizable monomers used for the polyaddition reaction may be any known monomers used for ordinary polyaddition reactions. Preferable monomers are those monomers capable of producing polyurethanes, polyurea resins, and epoxy resins.

Alcohol components used to prepare polyurethanes are compounds which have at least two hydroxyl groups in one molecule thereof. Specific examples of the alcohols include ethylene glycol, propylene glycol, butylene glycol, hexanediol, neopentyl glycol, polyethylene glycol, polypropylene glycol, polyoxytetramethylene glycol, glycerine, trimethylol propane, polyesters having two or more hydroxyl groups at ends thereof, and the like. The isocyanate components should have at least two isocyanate groups in one molecule thereof and specific examples of such isocyanates include tolylene diisocyanate, xylylene diisocyanate, hexamethylene diisoccyanate, 4,4'diphenylmethane diisocyanate, triphenylmethane triisocyanate, trimethylolpropane triisocyanate, and polyesters, polyethers and polyurethanes having two or more isocyanate groups at ends thereof.

The isocyanate components used to prepare polyurea resins may be such compounds as indicated above. The amine components should have at least two amino groups in one molecule thereof and specific examples of the amines include hexamethylenediamine, dodecyldiamine, phenylenediamine, diaminodiphenyl ether, piperidine and the like.

The epoxy components used to prepare epoxy resins should have at least two epoxy groups in one molecule thereof. Specific examples of the epoxy components include glycidyl ether compounds of bisphenol A, glycidyl ester compounds of dimer acids, and compounds obtained by oxidation of olefins. The amine components may be those amine compounds indicated above with respect to the polyurea. Hardening agents may be any known agents including, for example, tertiary amines, boron trifluoride-amine complexes, imidazoles, and other substances having functional groups capable of polyaddition reaction with epoxy groups such as amines, polyamines, carboxylic anhydrides, polysulfides, dicyandiamides, and diisocyanates.

The rod-shaped polymer lattices are prepared as follows. In order to produce polyurethane and polyurea resins, surface active agents are added to a reactor in which water is placed and agitated to solubilize an isocyanate component, followed by adding an aqueous solution of a diol or diamine. Alternatively, both components may be separately dissolved in organic solvents and the resulting solutions are solubilized in separate aqueous surface active agent solutions, followed by combining both solutions together. For the preparation of epoxy resins, a solution of a prepolymer or terminal epoxy compound and a hardening agent in solvents is gradually dropped into a hot aqueous solution of a surface active agent.

Where the monomers used above are solid or highly viscous liquid, it is preferred that they are dissolved in organic solvents and are solubilized in rod-shaped micelles along with the solvent, followed by polyaddition reaction. The organic solvents should be inert solvents which are insoluble in water and are incapable of reaction with other components. Preferable examples include benzene, toluene and xylene. The reaction temperature is a temperature such that a dynamic elastic modulus can be maintained in a reaction solution and is preferably in the range of from 20° to 70° C. The reaction time may vary depending on the type, composition and concentration of monomer and the reaction temperature, and is preferably in the range of from 1 to 50 hours.

It will be noted that phenolic resins which are polycondensates may be prepared similar to the above-described rod-shaped polymer lattices of eposy resins. For the preparation of the phenolic resin latices, phenol or phenolic derivatives such as cresol and formaldehyde are used. In addition, resol or novolac resins may be hardened by the use of acids or polyamines.

Rod-shaped polymer fine powders are prepared from the rod-shaped polymer lattices by removing water and, if necessary, surface active agents from the lattices.

Water and surface active agents can be removed from the latices by various techniques such as freeze-drying, centrifugal separation, precipitation with organic solvents miscible with water, precipitation by salting-out, and the like. The removal techniques should be determined depending on the use of the resulting powder. For instance, if surface active agents may be left in the powder, it is convenient to produce the fine powder by freeze-drying. On the other hand, if rod-shaped polymer fine powder is precipitated by addition of a solvent such as ethanol to the latex, surface active agents soluble in ethanol can be relatively easily removed. The powder from which the surface active agent has been removed is suitable as a powder for makeup cosmetics which are used in direct contact with the skin.

Non-aqueous media used to disperse the fine powder therein are selected depending on the type of final commercial product. Examples of such media include: monoalcohols, polyols and glycol ethers such as methanol, ethanol, glycerine, ethylene glycol and the like; nitriles such as acetonitrile, butyronitrile and the like; halogenated methanes and halogenated ethanes such as chloroform, bromoform and the like; ketones such as acetone, methyl ethyl ketone and the like; esters such as ethyl acetate, butyl acetate and the like; aromatic solvents such as benzene, toluene and the like; triglycerides such as castor oil, olive oil, rape oil and the like; and vaseline and paraffin.

[Effects of the Invention]

The rod-shaped polymer latex particles and fine powder thereof are substantially different in nature from odd-shaped lattices in which polymer cores are covered with a different type of polymer, and therefore have specific functions and properties which are different from those of the oddly-shaped latex particles prepared in the past.

The rod-shaped polymer lattices and powders can be applied to a wide variety of fields utilizing the structural anisotropy. For instance, they are useful as thickeners and paints in view of the high thixotropy of a dispersion. Because of the structural anisotropy of rod-shaped lattices, the lattices are useful as substrates for cosmetics such as lotions, creams, powders and the like. Moreover, the lattices whose particles are larger in specific surface area than known spherical latex particles are likely to adsorb proteins and can be used as a carrier for immunodiagnostics.

The dispersions of the rod-shaped polymer fine powders in non-aqueous media are relatively unlikely to coagulate and, when applied to the skin, they are smooth to the touch and are particularly useful as substrates for makeup cosmetics. The dispersion may further comprise cosmetic ingredients ordinarily used for the cosmetic purposes.

The present invention is described in more detail by way of examples and comparative examples, in which parts are by weight.

EXAMPLE 1

Into a 300 ml separatory four-necked glass flask equipped with an agitator were charged distilled water and each of various surface active agents indicated in Table 1 to prepare a viscoelastic solution, followed by complete substitution with nitrogen and heating to 60° C. to 75° C. while agitating. Thereafter, 20 parts of styrene and an aqueous solution of 0.5 part of ammonium persulfate serving as a radical initiator in 10 parts of distilled water were dropped in 2 hours while keeping the viscoelasticity. The viscoelasticity could be readily recognized because when the agitation was stopped, the solution turned in the reverse direction or swayed. The polymerization was carried out at 60° to 75° C. for further 6 hours.

One hundred parts of the resulting latex solution was charged into 200 parts of ethanol to allow precipitation of a gel-like latex. The solution was placed in a centrifuge tube and subjected to centrifugal separation at 1000 r.p.m. for 15 minutes. The resulting latex cake was again dispersed in ethanol, followed by repeating the centrifugal separation under the same conditions as used above. The thus obtained latex was dried to obtain a rod-shaped polystyrene powder. Scanning electron microphotographs exhibiting the particle structure of the rod-shaped polystyrene are shown in FIGS. 1 through 4. As will be clearly seen from the microphotographs, the latex has a rod-shaped form. The relation between dynamic elastic modulus of aqueous solutions of various surface active agents and shape of the resulting latices is shown in Table 1. The dynamic elastic modulus was determined as follows: a sample solution was placed in a double cylinder closed at one end thereof: and sine wave vibrations were applied to the outer cylinder whereupon a phase difference and an amplitude ratio of the sine wave vibrations transmitted to the inner cylinder were measured by a rheometer (Thixotrometer, by Iwamoto Seisakusho K.K.).

TABLE 1

Dynamic Elastic Modulus of Surface Active Agent Aqueous Solutions and Shape of Produced Latices

| Surface Active Agent | Parts | Dynamic Elastic[b] Modulus dyne/cm$^2$ | Shape |
|---|---|---|---|
| sodium hexadecenylsuccinate | 4 | 1.20 | rod |
| N,N—dimethyl-N—(carboxymethyl)octadecylammonium inner salt (0.5)[a] + sodium octadecylsulfate (0.5)[a] | 4 | 0.22 | rod |
| N,N—dimethyl-N—(3-sulfopropyl)octadecylammonium inner salt (0.3)[a] + sodium octadecylsulfate (0.7)[a] | 4 | 0.11 | rod |
| octadecyltrimethylammonium halogenated benzoate | 2 | 2.00 | rod |
| didodecylglycerine ether ethylene oxide adduct (the number of moles of added ethylene oxide: 20 moles) | 8 | 0.24 | rod |
| sodium dodecylsulfate | 0.2 | 0 | sphere |

[a]Mixing molar ratio.
[b]Frequency is 0.08 Hz.

EXAMPLE 2

Example 1 was repeated except that a solution of a surface active agent consisting of N,N-dimethyl-N-(carboxymethyl)octadecylammonium inner salt and sodium octadecylsulfate was used to polymerize styrene. The relation between mole fraction and shape of latex particles is shown in Table 2.

TABLE 2

Influences of mole Fraction of N,N—dimethyl-N—(carboxymethyl)octadecylammonium Inner Salt (A)

| Molar Fraction f | Dynamic Elastic Modulus dyne/cm$^2$ | Shape |
|---|---|---|
| 0.2 | 0 | sphere |

TABLE 2-continued

Influences of mole Fraction of N,N—dimethyl-N—(carboxymethyl)octadecylammonium Inner Salt (A)

| Molar Fraction f | Dynamic Elastic Modulus dyne/cm$^2$ | Shape |
|---|---|---|
| 0.3 | <0.01 | sphere |
| 0.4 | 0.17 | rod |
| 0.5 | 0.22 | rod |
| 0.6 | 0.18 | rod |
| 0.7 | 0.14 | rod |
| 0.8 | 0 | sphere |
| 0.9 | 0 | sphere | f = [A]/([A] + [sodium octadecylsulfate])

The dynamic elastic modulus is a value measured at a frequency of 0.08 Hz.

EXAMPLE 3

Example 1 was repeated using solutions of surface active agents including ethylene oxide adduct of α,α'-didodecylglycerine ether, octadodecyltrimethylammonium p-chlorobenzoate, and a mixture of N,N-dimethyl-N-(carboxymethyl)octadecylammonium inner salt and sodium octadecylsulfate. The relation between polymerization temperature and shape of latex particles is shown in Table 3 below.

TABLE 3

Influences of Polymerization Temperature

| Temperature °C. | A Dynamic Elastic (a) dyne/cm$^2$ | Shape | B Dynamic Elastic (b) dyne/cm$^2$ | Shape | C Dynamic Elastic (c) dyne/cm$^2$ | Shape |
|---|---|---|---|---|---|---|
| 40 | 0.25 | rod | 0 | sphere | 0.3 | rod |
| 50 | 0.25 | rod | 0 | sphere | 0.25 | rod |
| 60 | 0.22 | rod | 0.05 | rod | 2.30 | rod |
| 70 | <0.01 | sphere | 0.12 | rod | 0.05 | rod |
| 80 | 0 | sphere | 0 | sphere | 0 | sphere |
| 90 | 0 | sphere | 0 | sphere | 0 | sphere |

A: N,N—dimethyl-N—(carboxymethyl)octadecylammonium inner salt (mixing ratio: 0.5) + sodium octadecylsulfate (mixing ratio: 0.5),
B: ethylene oxide adduct of α,α'-didodecylglycerine ether (moles of added ethylene oxide: 20),
C: octadecyltrimethylammonium halogenated benzoate.
Frequencies: (a) 0.08 Hz, (b) 0.08 Hz, (c) 0.5 Hz.

EXAMPLE 4

The general procedure of Example 1 was repeated using sodium hexadecenylsuccinate (degree of neutralization: 0.7) and a monomer composition comprising 30 parts of styrene and 0.15 part of sodium styrenesulfonate. To the resulting solution was added triethanolamine, followed by heating and charging into ethanol as it is to give a coagulm. The coagulm was washed with hot ethanol several times and was then charged into distilled water while containing ethanol. After removal of the ethanol by distillation, there was obtained a dispersion comprising 14.5% of the latex. The viscosity of the rod-shaped latex was measured by means of the Brookfield viscometer, revealing that a ratio of viscosities at 3 r.p.m. and 30 r.p.m. was such that η3/η30=6.9, thus the thixotropy index being very high.

COMPARATIVE EXAMPLE 1

Figure 5:
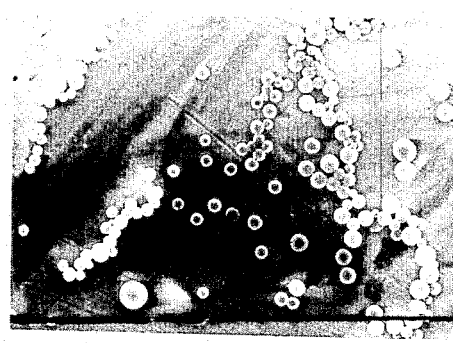
FIG. 5 is a microphotograph showing the structure of spherical latex particles obtained in Comparative Example 1.

In the same manner as in Example 1, the aqueous initiator solution and styrene were mixed at one time and the polymerization was conducted in the solution having little viscoelasticity. The microphotograph of the resulting latex solution is shown in FIG. 5. The latex particles were spherical and had an average size of 0.7 μm. As will be appreciated from the above, the polymerization in the solution having little viscoelasticity is an ordinary emulsion polymerization, so that spherical latex particles are formed.

COMPARATIVE EXAMPLE 2

Into a 500 ml separatory glass flask equipped with an agitator were charged 150 parts of distilled water, 3 parts of sodium dodecylsulfate, 0.5 part of ammonium persulfate, 100 parts of styrene, and 0.5 part of sodium styrenesulfonic acid, followed by complete substitution with nitrogen and heating to 80° C. under agitation. The polymerization was carried out for 8 hours to obtain a dispersion of spherical latex particles having an average size of 0.07 μm. The dispersion was dialyzed for 20 days using a cellophane dialysis membrane and distilled water, thereby removing the emulsifier. The resulting dispersion was diluted with distilled water to obtain a dispersion having a latex content of 14.5%. The viscosity of the dispersion was measured by the use of the B-type viscometer and was found to be 10 cps, showing no thixotropic properties.

EXAMPLE 5

In the same manner as in Example 1 using hexadecenylsuccinic acid as the surface active agent, styrene and sodium styrenesulfonate were polymerized. The results are shown in Table 4.

EXAMPLES 6, 7

The polymerization reaction was conducted in the same manner as in Example 1. Styrene and sodium styrenesulfonate were used as monomers in amounts indicated in Table 4 and 200 parts of 4% octadecyltrimethylammonium chlorinated benzoate was used as a surfactant. Thereby obtaining rod-shaped polystyrene/sodium sulfonate fine powder. The results are shown in Table 4.

EXAMPLE 8

Twenty parts of styrene and 0.25 part of sodium styrenesulfonate were used as polymerizable monomers and polymerized in the same manner as in Example 1. Sodium hexadecenylsuccinate was used as a surfactant, thereby obtaining a latex of polystyrene/sodium sulfonate. One hundred parts of the latex was immersed in an acetonedry ice bath and frozen, followed by sucking with a vacuum pump for freeze-drying for 24 hours to obtain a rod-shaped polystyrene/sodium sulfonate fine powder. The fine powder had an average size and a degree of wetting with water as shown in Table 4.

TABLE 4

Properties of Rod-shaped Polymer Fine Powder

| | Amount of Styrene (parts) | Amount of Sodium Styrenesulfonate (parts) | Average Particle Size (μm) | Wetting[a] to Water |
|---|---|---|---|---|
| Example | | | | |
| 1 | 20 | 0 | 4.0 ± 3 | -- |
| 5 | 20 | 0.125 | 3.6 ± 2 | - |
| 6 | 20 | 0.25 | 10.6 ± 2 | + |
| 7 | 20 | 1.25 | 9.5 ± 2 | ++ |
| 8 | 20 | 0.25 | 3.8 ± 2 | ++ |
| Comparative Example | | | | |
| 3 | Kaolin | | 0.1–10 | ++ |

TABLE 4-continued

Properties of Rod-shaped Polymer Fine Powder

| Amount of Styrene (parts) | Amount of Sodium Styrene-sulfonate (parts) | Average Particle Size (μm) | Wetting[a] to Water |
|---|---|---|---|
| 4 | Wollastonite | 5–500 | ++ |

[a] — —: complete water repellency, —: slight water repellency, +: slight wetting, ++: complete wetting
The values of the monomers are by parts.

EXAMPLE 9

Rouge

| | | |
|---|---|---|
| (1) Titanium dioxide | 2.0 (wt %) | |
| (2) Red No. 204 | 2.5 | |
| (3) Red No. 220 | 0.5 | |
| (4) Yellow No. 4 Al lake | 0.2 | |
| (5) Rod-shaped polystyrene fine powder (obtained in Example 5) | 8.0 | |
| (6) Cetyl lactate | 10.0 | |
| (7) Lanoline | 5.0 | |
| (8) Castor oil | 52.7 | |
| (9) Carunauba wax | 2.0 | |
| (10) Candelilla wax | 8.0 | |
| (11) Ceresin wax | 4.0 | |
| (12) Beeswax | 4.0 | |
| (13) Perfum | suitable amount | |
| (14) Antioxidant | suitable amount | |

Ingredients (1) through (4) were added to part of the castor oil to obtain a uniform pigment composition. The other ingredients were heated and melted, followed by mixing with the pigment composition and uniformly dispersing in a homogenizer. After the dispersion, the dispersion was poured into a mold and cooled to obtain rouges which were able to apply uniformly and rarely suffered color drifting.

What is claimed is:

1. A rod-shaped polymer latex which comprises latex particles having a major axis of from 0.1 to 100 μm and a minor axis of less than ⅓ the major axis, an aqueous dispersion of the particles at a concentration of not larger than 15 wt % having a thixotropy index, η3/η30, of not less than 1.5 in which η3 and η30, respectively, represent viscosities when measured by means of the Brookfield viscometer at 3 and 30 r.p.m.

2. A rod-shaped polymer fine powder having a major axis of from 0.1 to 100 μm and a minor axis of less than ⅓ the major axis.

3. A dispersion comprising a rod-shaped polymer fine powder having a major axis of from 0.1 to 100 μm and a minor axis of less than ⅓ the major axis and dispersed in a non-aqueous medium.

4. The dispersion according to claim 3, further comprising cosmetic materials.

5. A process for producing a rod-shaped polymer in fine powder form having a major axis of from 0.1 to 100 μm and a minor axis of less than ⅓ the major axis, which comprises:
  solubilizing a polymerizable monomer in an aqueous surface active agent containing solution which has a dynamic elastic modulus of not less than 0.01 dyne/cm² in a frequency range of from 0.05 Hz to 1.0 Hz;
  initiating the polymerization reaction in water;
  continuing the polymerization reaction while adding monomer at such a rate that the dynamic elastic modulus of the aqueous surface active agent containing solution is within the above-defined range; and
  removing water from said solution.

6. The process of claim 5, wherein surface active agent is removed from said rod-shaped polymer particles upon removal of water.

7. The process of claim 6, wherein the polymerizable monomer is a vinyl monomer or an acrylic monomer.

8. The process of claim 5, wherein said aqueous solution has a dynamic elastic modulus ranging from 0.5 to 10 dyne/cm².

9. The process of claim 5, wherein the surface active agent in said aqueous solution is a surface active agent selected from the group consisting of
(a) a compound of the formula:

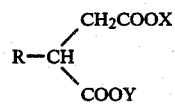

wherein R represents a hydrocarbon group having from 6 to 24 carbon atoms, and X and Y independently are each hydrogen, an alkali metal, ammonium, an alkanolamine having from 2 to 3 carbon atoms, or a basic amino acid,
(b) a compound of the formula:

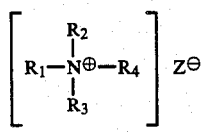

wherein $R_1$ is a hydrocarbon group having from 8 to 24 carbon atoms, $R_2$, $R_3$ and $R_4$ independently each represent a hydrocarbon group or a hydroxyhydrocarbon group having from 1 to 3 carbon atoms, or a benzyl group, and $Z^\ominus$ represents a counter anion,
(c) a compound of the formula:

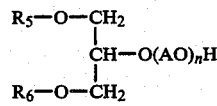

or

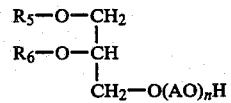

wherein $R_5$ and $R_6$ independently each represent a hydrocarbon group having from 6 to 24 carbon atoms, n is an integer of from 1 to 50, and A is a hydrocarbon group having from 2 to 4 carbon atoms,
(d) a surface active composition comprising the following two ingredients (A) and (B) in a ratio by weight of 100:20 to 30:100,
(A)
  (1) $RSO_3X_1$
  (2) $RSO_4X_1$
  (3) $RO(AO)_{n1}SO_3X_1$, or (4) 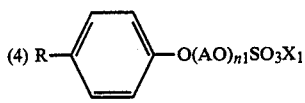

wherein R represents a hydrocarbon group having from 6 to 24 carbon atoms, $n_1$ represents an integer of from 1 to 20, A represents a hydrocarbon group having from 2 to 4 carbon atoms, $X_1$ represents ammonium, an alkali metal, an alkaline earth metal, an alkanolamine having from 2 to 3 carbon atoms, or a basic amino acid (B)

(1) 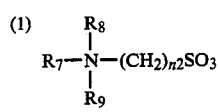

(2) 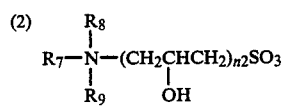

(3) 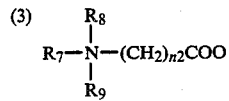

(4) 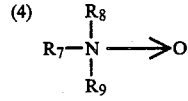

or (5) 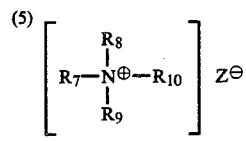

wherein $R_7$ represents a hydrocarbon group having from 6 to 24 carbon atoms, $R_8$, $R_9$ and $R_{10}$ independently each represent a hydrocarbon group or hydroxyhydrocarbon group, each having from 1 to 3 carbon atoms, or a benzyl group, $n_2$ is an integer of from of from 1 to 10, and $Z^\ominus$ represents a counter anion, (e) a compound of the formula:

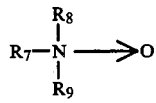

wherein $R_7$, $R_8$ and $R_9$ are each as defined above, and (f) a compound of the formula:

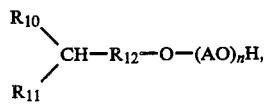

wherein $R_{10}$ is a $C_6$-$C_{24}$ hydrocarbon group, $R_{11}$ is a $C_1$-$C_{24}$ hydrocarbon group, $R_{12}$ is a $C_{1-4}$ hydrocarbon group and A and n each have the meanings defined above.

* * * * *